(12) United States Patent
Scharnweber et al.

(10) Patent No.: US 7,585,965 B2
(45) Date of Patent: Sep. 8, 2009

(54) METALLIC OBJECT WITH A NUCLEIC ACID COATING AND DERIVATIVES THEREOF AND METHOD FOR PRODUCING SAID OBJECT

(75) Inventors: Dieter Scharnweber, Dresden (DE); René Beutner, Dresden (DE); Sophie Roessler, Dresden (DE); Thomas Hanke, Berlin (DE); Hartmut Worch, Dresden (DE); Bernd Schwenzer, Bannewitz (DE); Jan Michael, Dresden (DE)

(73) Assignee: Technische Universität Dresden, Dresden (DE)

( * ) Notice: Subject to any disclaimer, the term of this patent is extended or adjusted under 35 U.S.C. 154(b) by 249 days.

(21) Appl. No.: 10/519,988

(22) PCT Filed: Jul. 4, 2003

(86) PCT No.: PCT/DE03/02305

§ 371 (c)(1),
(2), (4) Date: Jul. 25, 2005

(87) PCT Pub. No.: WO2004/005306

PCT Pub. Date: Jan. 15, 2004

(65) Prior Publication Data

US 2006/0035229 A1    Feb. 16, 2006

(30) Foreign Application Priority Data

Jul. 4, 2002    (DE) ................ 102 32 139

(51) Int. Cl.
*C12Q 1/68* (2006.01)
*C07H 21/02* (2006.01)
*C07H 21/04* (2006.01)

(52) U.S. Cl. .............. 536/24.33; 435/6; 536/23.1; 536/24.3

(58) Field of Classification Search ............ None
See application file for complete search history.

(56) References Cited

U.S. PATENT DOCUMENTS 6,169,194 B1 * 1/2001 Thompson et al. .......... 556/429
6,232,075 B1 * 5/2001 Williams ..................... 435/6
6,291,188 B1    9/2001 Meade et al.
6,406,852 B1    6/2002 Tuli et al.
6,524,718 B1 * 2/2003 Worch et al. ................ 428/472
6,670,461 B1 * 12/2003 Nielsen et al. .............. 536/23.1
2003/0186914 A1    10/2003 Hofer et al.

FOREIGN PATENT DOCUMENTS

| DE | 4309248 | 9/1994 |
|---|---|---|
| EP | 0 391 608 A2 * | 10/1990 |
| EP | 1230015 A1 | 8/2002 |
| WO | WO 85/02628 A1 * | 6/1985 |
| WO | WO 9817844 A1 * | 4/1998 |

OTHER PUBLICATIONS

Bier, F.F., and Scheller, F.W.: Label-free observation of DNA-hybridisation and endonuclease activity on a wave guide surface using a grating coupler; Biosensors & Bioelectronics, 1996, vol. 11; pp. 669-674.
Bier, F.F., et al.: Changing Functionality of Surfaces by Directed Self-Assembly Using Oligonucleotides—The Oligo-Tag; Biotechniques, 1999, vol. 27, pp. 752-760.
Xiao, S.J. et al.,: Covalent Attachment of Cell-Adhesive, (Arg-Gly-Asp)-Containing Peptides to Titanium Surfaces; Langmuir, 1998; vol. 14, pp. 5507-5516.
Agarwal, S. (editor), Methods in Molecular Biology 26: Protocols for Oligonucleotide Conjugates, 1994, Humana Press Inc., Totowa NJ, USA).

* cited by examiner

*Primary Examiner*—Young J Kim
(74) *Attorney, Agent, or Firm*—Gudrun E. Huckett

(57) ABSTRACT

A metallic object has a coating made of a thin metal oxide layer and nucleic acids or nucleic acid derivatives bonded thereto. The nucleic acid compounds have 5'-terminal or 3'-terminal molecule areas that are incorporated stably into the metal oxide layer. The unincorporated areas of the nucleic acid compounds that are not incorporated into the metal oxide layer are freely accessible for subsequent interactions with other molecules such as complementary nucleic acids having active ingredients attached thereto.

20 Claims, 1 Drawing Sheet

METALLIC OBJECT WITH A NUCLEIC ACID COATING AND DERIVATIVES THEREOF AND METHOD FOR PRODUCING SAID OBJECT

BACKGROUND OF THE INVENTION

The invention relates to a metallic object comprising a stable coating of nucleic acid compounds, i.e. nucleic acids and/or nucleic acid derivatives, and a method for manufacturing aforementioned coating. By coupling active ingredients to the nucleic acids and/or nucleic acid derivatives, the coating can be matched to different applications and the biocompatibility of surfaces modified accordingly can be increased.

Such coated metals are of interest for the medical field and veterinary medicine, for example, for implants but also for different fields of biotechnology as well as chip and sensor technology.

An efficient immobilization of nucleic acids and nucleic acid derivatives on solid support materials is of great importance for many areas of biotechnology.

Methods for the immobilization of nucleic acids on glass, for example, for producing nucleic acid arrays, as well as for the immobilization of gold pobjects (U.S. Pat. No. 6,291,188 B1, EP 1170374 A1), for example, for gene transfer, are known. The immobilization of gold pobjects is realized in this context either by adsorption (EP 1170374 A1) or by a sulfur linker (U.S. Pat. No. 6,291,188 B1).

Moreover, methods for adsorption of nucleic acids on zirconium(IV) oxide and aluminum oxide and other metal oxides are disclosed (DE 4309248 A1, EP 0391 608 A2, WO 92/18514 A1). In order to ensure this adsorption on the aforementioned metal oxides, the material, however, must be comprised of at least 50%, preferably 99%, of metal oxide (EP 0391 608 A2, p. 4, lines 18-29).

For numerous applications, an oriented, reproducible, permanent, fixed, chemical and temperature-resistant bonding of the nucleic acids and/or nucleic acid derivatives on the substrate surface is desirable.

Disclosed are also methods for bonding oligonucleotides on valve metals, for example, silanized tantalum (Bier, F. F., and Scheller, F. W., 1996, Biosensors & Bioelectronics 11:669-674) and silanized titanium (Bier, F. F., et al., 1999, Biotechniques 27:752-760). In order to achieve the silanization of the metal surface required for this method, the metal must be pretreated under aggressive chemical conditions (see also Xiao, S. J. et al., 1998, Langmuir, 14:5507-5516). Disadvantageously, these methods are comprised of at least three steps. In addition, the nucleic acids must also be modified in a complex procedure.

Methods are know that ensure a fixed connection of organic molecules, for example, collagen, on valve metal surfaces (DE 19643555). Oxide layers that are formed on such metals or alloys exhibit ion conduction at least under anodic polarization and enable thus by means of anodic polarization a variation of oxide layer thickness within wide limits. For this purpose, the phenomenon that for anodic polarization in aqueous solutions the already present oxide layer on titanium materials begins to grow by migration of ions within the electric field is utilized. Into this growing layer, molecules or functional groups that are present on the surface, for example, as a result of adsorption can be incorporated into the oxide layer. However, an oriented incorporation by means of defined molecular areas (regiospecific incorporation) of substances and thus maintaining certain properties/functions of the substances cannot be realized.

It is known in connection with inorganic ions, primarily phosphate, that they can be incorporated into such anodically growing titanium(IV) oxide layers. In this connection, the anion can possibly also be part of larger molecules (DE 19643555) as a functional group. In order for the molecule provided with the anionic group to be incorporated into the anodic oxide layer, the electrostatic charge conditions between surface and adsorbing molecule (part) must allow a primary adsorption.

Negatively charged molecules, such as nucleic acids, are however repelled by the titanium-titanium(IV) oxide surface that is negatively charged under physiological conditions. The method described in DE 19643555 is therefore not applicable in connection with nucleic acid molecules.

A general disadvantage of the chemically or biochemically modified surfaces employed in medicine, biology, and chemistry is the lack of variability and modularity. Substances that have been applied once remain in many cases irreversibly attached to the surfaces or have a release kinetics adjustable only to a limited extent. Moreover, the coating process must be matched often in complex ways to the desired coating. It is therefore almost impossible for a user to match a coating to his applications.

SUMMARY OF THE INVENTION

The object of the invention is to provide a metallic object with a stable coating of nucleic acid compounds, i.e. nucleic acids and/or nucleic acid derivatives, in which the nucleic acids are optimally accessible for further reactions, for example, hybridizations.

According to the invention, the object is solved by a metallic object whose surface is covered with a thin metal oxide layer and is coated with nucleic acids or nucleic acid derivatives, wherein 5'-terminal or 3'-terminal molecule areas of nucleic acids are stably incorporated into the metal oxide layer.

The term thin metal oxide layer is to be understood in this connection such that the metal oxide layer is at least thinner than the average diameter of the metallic object.

When in the following the term nucleic acid is mentioned, this term includes, as a matter of principle, nucleic acid derivatives.

In particular, in the context of this specification, nucleic acids are to be understood as the following molecules: desoxyribonucleic acids (DNA), ribonucleic acids (RNA), and peptide nucleic acids (PNA) as well as all modifications that can be derived from these basic structures, for example, phosphothioates, phosphoamidates, O-methyl derivatives and locked nucleic acids (LNA). The nucleic acids can be single strands, double strands, or mixed structures thereof. Preferably, in the case of a coating with double strand DNA only one of the nucleic acid strands is bonded fixedly to the metal-metal oxide surface (substrate surface).

The stable incorporation of 5'-terminal or 3'-terminal molecule areas into the metal oxide layer is achieved by the method according to the invention wherein electrochemically a metal oxide layer is built up about the molecule areas. The stable incorporation results from the integration of the terminal molecule areas into the growing metal oxide layer.

With this regiospecific incorporation of the terminal molecule areas, a freely movable orientation of the areas of the unincorporated nucleic acids relative to the metal surface is achieved. Because of the free movability, the unincorporated areas of the nucleic acids advantageously are accessible optimally for subsequent processes, for example, hybridization with a complementary strand.

A further advantage is that all immobilized nucleic acids molecules are thus incorporated regiospecifically into the oxide layer. In this way, a surface results that is coated with uniform orientation.

This regiospecific reproducible and fixed incorporation of the terminal molecule areas into the metal oxide layer is not achievable by the adsorption of nucleic acids known in the prior art.

According to the invention, the incorporated 5'-terminal or 3'-terminal areas of the nucleic acids have anionic groups, preferably phosphate, phosphonate, or sulfate.

The metallic object is comprised preferably of a valve metal, for example, aluminum, titanium, tantalum, zirconium, niobium, or their alloys, including intermetallic phases.

The sequences of the nucleic acids immobilized at the 5'-terminal molecule areas are advantageously selected such that the sequences that are relevant for subsequent processes, for example, hybridization, are still accessible even after a layer growth of more than 2 nm. The sequences in the direct vicinity of the 5'-terminal are freely selectable because they are incorporated into the oxide layer. On the other hand, the sequences in the vicinity of the freely movable 3'-terminal molecule areas advantageously comprise specific recognition sequences, for example, for a subsequent hybridization with complementary strands.

The same holds true also for nucleic acids immobilized on the 3'-terminal molecule areas.

In a particularly advantageous embodiment of the metallic object according to the invention on whose surface single strand nucleic acids are immobilized, complementary nucleic acid single strand molecules are bonded thereto by means of Watson-Crick and other base pairs. The sequence of the immobilized strand determines which sequence(s) can complementarily bond thereto.

According to the invention, different biological or chemical active ingredients can be covalently bonded to the complementarily bonding nucleic acid strands. Advantageously, the biological and chemical properties of the correspondingly modified surface is determined primarily by the active ingredients coupled to the nucleic acids.

Bonding of the complementary strands can advantageously be performed also by the user. By selecting complementary strands with suitable active ingredients it is possible for the user to match the biological and chemical properties of the metal surface to the specifications that are required for his special application.

The modularity of this system ensures thus an almost unlimited variability for building "biologized" surfaces.

The active ingredients are, for example, inorganic or organic or biochemical molecules or cell components or tissue components.

In this connection, based on a metallic object that is coated with single strand nucleic acids, the biological properties of the surface can be varied by the subsequent factors in multiple ways:

The sequences of the immobilized strands determine which nucleic acid sequences can be bonded complementarily.

The stability of the bond between the immobilized and complementary strands determines the release behavior and the resulting bioavailability of active ingredients bonded thereto.

On immobilized strands with same sequence, complementary strands that have different active ingredients can bond.

Different nucleic acids can be simultaneously immobilized in a laterally defined or statistically distributed arrangement on the immobilized strands, with identical flexibility with regard to the design of the properties described in the three items listed above.

By a variable design of the hybridization on one and the same surface, the release behavior of the nucleic acids that are associatively bonded and have complementary active ingredients can be controlled.

By modification of the bases, for example, inosine, or of the backbone of the nucleic acids, for example, a peptide backbone, a phosphothioate backbone, or methyl phosphonate backbone, the chemical stability and the stability relative to decomposition by nucleases can be influenced in a targeted way. The above-mentioned properties are not affected significantly by this.

The sequence of the immobilized nucleic acids can comprise special recognition sequences for antibodies, nucleic acid bonding proteins or nucleases.

The stability of the bond between immobilized and complementary strands essentially depends on the length of the hybrid area, its G-C contents, and the number of so-called "mismatches", i.e., non-complementary base pairs. In this connection, the stability increases with the proportion of G-C as a result of a greater number of hydrogen bonds (G-C pairs: three hydrogen bonds; A-T pairs: two hydrogen bonds). Mismatch pairs do not form hydrogen bonds because they are not complementary. The greater the number of mismatches, the less stable the hybrid.

If the release of the complementary strands and the active ingredients coupled thereto is not desired, this can be prevented advantageously by covalent bonding of the complementary strand to the immobilized strand. Such a covalent bond can be achieved, for example, by cross-linking with UV light or chemical reactions.

If an especially fast release of the active ingredients bonded to the complementary strands is desirable in a biological medium, this can be achieved by incorporating recognition sequences for nucleases.

The object that is coated according to the invention with nucleic acids distinguishes itself by the following important advantages from objects that are coated by other methods with nucleic acids:

The stability of the nucleic acid coatings.

A as a result of the regiospecific fixation of the nucleic acids on the terminal molecule areas, an optimal accessibility for subsequent processes, for example, hybridization, results.

The stability of immobilization and the length of the unincorporated areas of the nucleic acids depend on the thickness of the metal oxide layer into which the terminal molecule areas of the nucleic acids are incorporated. This layer thickness can be controlled advantageously by means of the method according to the invention.

Possibility for variable and modular modification of the metal surface by bonding complementary strands and active ingredients bonded to the latter.

Possibility of influencing the release behavior and thus the bioaccessibility of the active ingredients by the molecular structure of the nucleic acid hybrid.

Possibility of simple adaptation of the coatings by the user.

According to the invention, the metallic object coated with nucleic acids is produced by a method in which the nucleic acids provided with anionic groups at least at one terminal molecule area is contacted with the metallic object in such a way that the nucleic acids are initially metastably present on the metal oxide surface as a result of a regiospecific interaction. Simultaneously or subsequently, the metallic object is polarized anodically in an electrolyte solution. By anodic polymerization, a multi-layer oxide layer is produced, and, into its outer layer, the molecule areas of the nucleic acids that have terminal anionic groups are stably incorporated.

Surprisingly, it was found that a terminal modification of the nucleic acids with anionic groups of a suitable pKs value enables the immobilization of nucleic acids. In this connection, the anionic groups are comprised of molecule structures that exhibit a negative charge at the pH value and the ion strength according to the method. Preferably, the anionic groups are phosphate or phosphonate or sulfonate groups. The bond of the anionic groups to the terminal molecule areas is realized preferably covalently on the 3'-terminals or 5'-terminals of the nucleic acids.

Advantageously, terminal (end position) phosphorylated oligonucleotides are commercially available.

According to the invention, the incorporation of the nucleic acids begins at the terminal anionic group and is essentially determined by it. In contrast to terminal phosphate groups, the phosphate groups of the nucleic acid backbone are not suitable to initiate incorporation into the metal oxide layer (see example 4). The phosphate groups within the DNA backbone can therefore be replaced by other bond types, for example, peptide, phosphothioate, methyl phosphonate or others.

According to the invention, the conditions for the immobilization are selected such that the anionic groups carry at least one negative charge while the metal-metal oxide surface at least has some local positive charge centers. Under these conditions, an electrostatically initiated adsorptive bonding of the terminal areas of the nucleic acids on the positive charge centers of the oxide surface is enabled.

According to the invention, the adsorptive bonding and the subsequent incorporation by anodic polarization is realized at pH 3 to 6, preferably at pH 4, in acetate buffer.

The growth of the oxide layer can be controlled by the selection of the electrochemical parameters, preferably potential, current density, and velocity of potential change. In this connection, the electrochemical parameters determine the occurring depth of incorporation and the size of the molecules determines the permissible depth of incorporation.

Preferably, for the achieved potential a value between 2 and 200 $V_{SCE}$ is selected. This potential ensures advantageously a sufficiently stable incorporation of the nucleic acids into the oxide layer and prevents at the same time growth of the oxide layer into a recognition area of the nucleic acid required, for example, for later hybridization.

After immobilization, the generated matrix is rinsed with a buffer (pH approximately 4) and distilled water. The sample can be immediately processed further or can be stored dried at cool temperatures (<10° C.) under exclusion of light.

Surprisingly, as a result of the immobilization according to the invention, a free accessibility of the unincorporated sections of the immobilized nucleic acid strand is obtained. Accordingly, the unincorporated portion of the nucleic acid is optimally available for subsequent processes, for example, hybridization with a complementary strand.

For a possible subsequent hybridization of complementary nucleic acid strands on the metal that is coated with single strand nucleic acids, the conditions must be selected such that a best possible interaction and thus formation of sufficiently stable hybrids between the immobilized individual strands and the individual strands in solution takes place.

For the hybridization to be performed after immobilization, the pH value and the ion strength are selected such that the metal-metal oxide surface as well as the nucleic acid backbone are negatively charged and, in this way, an electrostatic repelling action between the DNA backbone and the metal-metal oxide surface is achieved, while the stable immobilization of the nucleic acids by means of its terminal incorporation into the oxide layer is maintained however. In the case of nucleic acid derivatives with uncharged backbone, the conditions are selected such that the metal-metal oxide surface is negatively charged. Because of the repelling action away from this surface, freely movable orientation of the immobilized strands is enhanced and an unspecific adsorption of complementary strands that would cause impairment of hybridization is prevented.

As a function of the length and base composition of the sequences to be hybridized, a buffer system of suitable ion strength, conventionally in the range between 0.1 and 1.5 mol/liter of monovalent cations, is selected. The pH value of the hybridizing solution according to the invention is between pH 4 to pH 10, preferably between pH 5.5 and pH 8.5, particularly preferred between pH 7.0 and pH 7.5. In the hybridizing solution, the complementary strands are present to which inorganic, organic, primarily bioactive groups or molecules are bonded. This bond is preferably of a covalent nature in an alternative configuration, bonding of the molecules to the complementary strands is realized by a biotin/avidine or streptavidine bond.

For hybridization, the surface of the metallic object that is coated with single strand nucleic acids is incubated between 10 minutes and 2 hours with the described hybridization solution and subsequently rinsed with buffer solution and water.

Advantageously, the conditions for hybridization are mild and can be selected such that they correspond almost to physiological conditions. In this way, the best possible molecular and functional integrity of the biological active ingredients that are bonded to the complementary strands is ensured.

If no direct subsequent application is carried out, the object coated in this way can be stored at cool temperatures (<10° C.) under exclusion of light.

Advantageously, the hybridization and thus the coating with the desired active ingredients can be realized shortly before being used by the user. This enables the best possible flexibility and immediate decisions in regard to the selection of active ingredients as well as a separate storage of metallic object and active ingredients.

Coupling of the active ingredients on the nucleic acids can be realized by means of functional groups, for example, amino alkyl or mercapto alkyl groups, bonded terminally to the nucleic acids (s. Agarwal, S. (editor), 1994, Methods in Molecular Biology 26: Protocols for Oligonucleotide Conjugates, Humana Press Inc., Totowa N.J., USA). Nucleic acids modified with such functional groups, for example, amino hexyl, are commercially available. Active ingredients can be bonded by means of commercially available cross-linking agents through these functional groups to the nucleic acids. Commercially available are also nucleic acids terminal-modified by biotin. Avidine-conjugated or streptavidine-conjugated active ingredients can be bonded to the latter.

In a special embodiment of the nucleic acid-coated object, organic or inorganic groups that contain radioactive elements are bonded to the nucleic acid strands. A system modified in this way is suitable for medical-analytical purposes (scintigraphy etc) and for therapeutic purposes (local radiation therapy of tumors).

The method according to the invention is distinguished by the following important advantages from known methods:
 Stable immobilization of nucleic acids.
 Targeted design of a desired depth of incorporation of the fixed nucleic acid into the surficial oxide layer is possible.

It can also be used in connection with nucleic acid derivatives.

Only one method step required for immobilization of the nucleic acids.

No toxic chemicals for immobilization are required.

Inexpensive and easily applicable, controllable, adaptable for automation, suitable for industrial production.

Regiospecific terminal incorporation of nucleic acids.

Generation of reproducible and substantially identical immobilization states of the individual molecules is enabled. In this way, a very homogenous behavior of the immobilized nucleic acids for subsequent hybridization as well as homogeneity in regard to the stability of the thus generated hybrids is achieved.

When employing the coated metallic object according to the invention for use in implants in the medical field, the aforementioned variation possibilities enable the alternative or simultaneous coating of the implant with substances of different biological effectiveness, for example, specific growth factors, messenger agents and antibodies.

Advantageously, the release behavior of these active ingredients can be affected by variations in the hybrid stability. The simultaneous or temporally shifted release of one or several active ingredients from one and the same surface is enabled in this way.

A conceivable medical application is the osteoinductive coating of an implant surface for bone contact with the "bone morphogenetic protein" type 4 (BMP-4) as an active ingredient coupled to the nucleic acids.

A different application possibility is the coating of the implant surface with the growth factor TGF-β (tissue growth factor beta) that positively affects cell proliferation and cell differentiation as an active ingredient coupled to the nucleic acids.

In a special embodiment of the method, organic or inorganic groups containing radioactive elements are bonded to the nucleic acid strands. A system modified in this way is suitable for medical-analytical purposes (scintigraphy etc) and for therapeutic purposes (local radiation therapy of tumors).

DESCRIPTION OF PREFERRED EMBODIMENTS

With the aid of the following examples the invention will be explained in more detail. One embodiment variant of the solution according to the invention is explained in Example 1. The additional examples are negative examples.

The DNA oligonucleotides used in the following examples were obtained from the company SIGMA-ARK GmbH, Darmstadt, and have the following sequences:

T3E-5P:
$^{2-}O_3PO$-5'-CCA AAC CCG TCA ATC AAG TCT ACA CTG TTC-3'

T3E-5NH2:
$H_2N$-5'-CCA AAC CCG TCA ATC AAG TCT ACA CTG TTC-3'

S3E-FI:
fluorescein-HN-$(CH_2)_6$-5'-CAG TGT AGA CTT GAT-3'

EXAMPLE 1

1a.) Pretreatment

A cylindrical sample of TiAl6V4 having a diameter of 10 mm and a thickness of 3 mm was ground, oxide polished, and washed with ethanol.

The thus pretreated sample of TiAl6V4 is introduced as a substrate electrode into a three-electrode arrangement with a silver/silver chloride electrode as a reference electrode and a platinum counter electrode in a well of a cell culture dish.

A solution of 400 nmol/liter of 5'-phosphorylated T3E-5P DNA in sterile acetate buffer (0.2 mol/liter, pH=4) is denatured at 95° C. and is placed on ice for at least 5 minutes.

After connecting all electrodes to the potentiostat/galvanostat unit, 3 ml of the prepared DNA solution are introduced into the well of the cell culture dish and incubated for 15 minutes at room temperature without supplying voltage.

Figure 1:
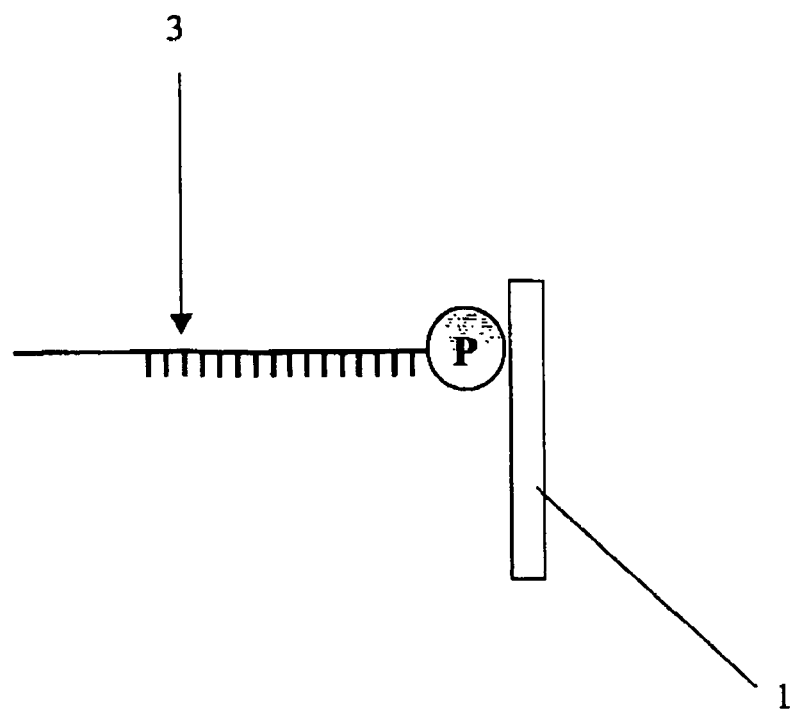
FIG. 1 shows schematically a nucleic acid molecule fixed metastably on the substrate surface comprised of a thin metal-metal oxide layer.

As illustrated schematically in FIG. 1, by means of this pretreatment individual nucleic acid molecules 3 are fixed metastably onto the substrate surface 1 that is comprised of a thin metal-metal oxide layer. In order to simplify the illustration, only one nucleic acid strand is illustrated. The bases of the nucleic acids are illustrated by vertical lines on the continuous line of the nucleic acid backbone.

1b.) Anodic Polarization

Subsequently, the TiAl6V4 sample is anodically polarized at a current density of 76 $\mu A*cm^{-2}$ for 2 minutes. The potential is limited to maximally 10 V relative to the Ag/AgCl reference electrode. When this value is reached, the immobilization is stopped prematurely.

After completion of the electrochemical polarization, the cell culture dish with the titanium sample is rinsed with 3 ml sterile acetate buffer (0.2 mol/liter, pH=4.0) and subsequently rinsed twice with 3 ml sterile water.

Figure 2:
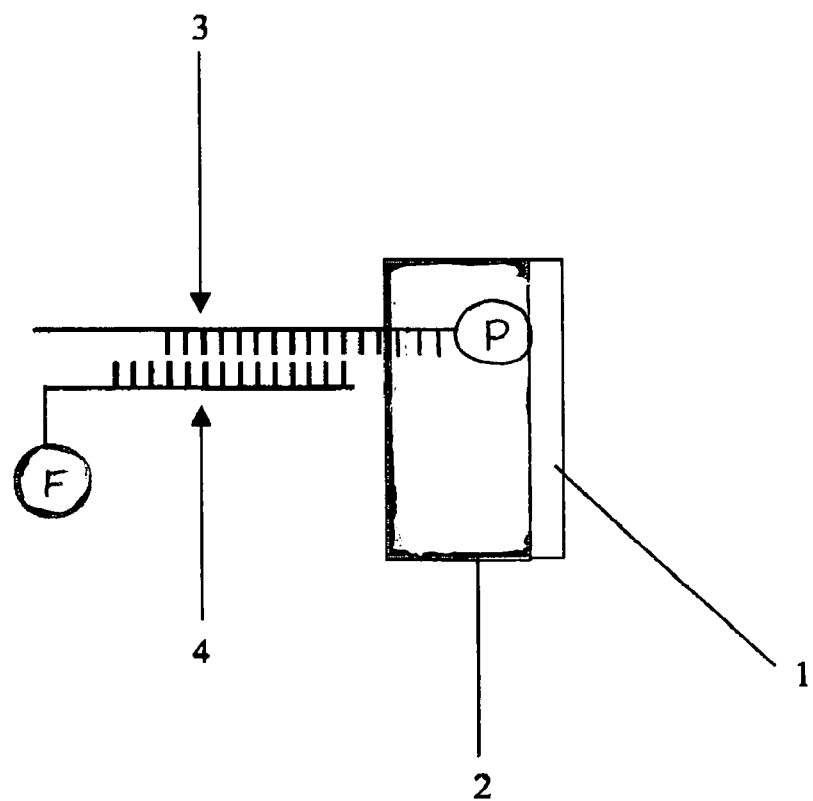
FIG. 2 shows schematically a newly grown metal oxide layer that is produced by anodic polarization and has embedded therein the terminal area of the nucleic acid molecule of FIG. 1; also shown is the complementary fluorescein-marked nucleic acid compound bonded to the immobilized nucleic acid compound.

As a result of the anodic polarization the already present metal oxide layer 1 grows in thickness by the portion 2. This portion 2 of the metal oxide layer newly formed by the anodic polarization embeds in this connection the terminal area of the DNA molecules (FIG. 2).

1c.) Hybridization

For hybridization, a solution of DNA (S3E-FI DNA) 4 that is complementary to the 3'-terminal of the DNA strands 3 (T3E-5P DNA) immobilized by anodic polarization is prepared as follows:

A solution of 40 nmol/liter of S3E-FI DNA and sterile TRIS-HCl buffer (50 mmol/liter; pH=7.5) is denatured at 95° C. and is subsequently immediately placed on ice for at least 5 minutes.

With 3 ml of the solution prepared in this way the sample is incubated for 1 hour and subsequently rinsed once with TRIS- HCl buffer (50 mmol/liter; pH=7.5) and twice with 3 ml sterile water and is then air-dried in a sterile and dust-free environment.

A sample treated in this way shows in fluorescence microscopy a strong fluorescence on the metal surface in the green wavelength range. This proves a successful stable immobilization of the 5'-phosphorylated T3E-5P DNA on the metal-metal oxide surface as well as a successful hybridization with the complementary S3E-Fl DNA.

FIG. 2 shows schematically the surface of such nucleic acid coated metallic object with a thin metal oxide layer 1 into which layer in this case the 5'-terminal areas of nucleic acid molecules 3 with the 5'-terminal phosphate groups P are stably incorporated within the second metal oxide layer 2 built up by anodic polarization. In order to simplify the illustration, only one nucleic acid strand (in this example T3E-5P DNA) is illustrated. By means of complementary base pair bonding, the corresponding fluorescence-marked F counter strand 4 (in this example S3E-Fl DNA) is bonded to its molecule area that is not incorporated into the oxide layer.

EXAMPLE 2

A metallic sample of TiAl6V4 is incubated as described in Example 1 with a 5'-phosphorylated T3E-5P DNA (see 1a) and subsequently rinsed with 3 ml sterile acetate buffer (0.2 mol/liter; pH=4.0) and twice with 3 ml sterile water without performing anodic polarization (see 1 b). Subsequently, the sample is incubated, as described in Example 1, with fluorescent S3E-Fl DNA that is complementary to the 3'-terminal of T3E-5P DNA and is then washed.

No fluorescence could be found in fluorescence microscopy for a sample treated in this way. Since this Example matches exactly Example 1, with the exception of the step of anodic polarization, this demonstrates that in contrast to the method according to the invention (Example 1) no stable bonding of DNA can be achieved by means of pure adsorption to the already present metal oxide surface.

EXAMPLE 3

This is carried out in the same way as Example 2 with the difference that the sample of TiAl6V4 is incubated only with the fluorescent S3E-Fl DNA and not prior to this with T3E-5P DNA.

Fluorescence microscopy shows no fluorescence in a sample treated in this way.

Example 3 shows that even nucleic acids that are marked with fluorescein cannot be immobilized in detectable quantities by adsorption on an oxide layer already provided on a TiAl6V4 surface.

EXAMPLE 4

This is carried out in the same way as Example 1 with the difference that for anodic polarization instead of the 5'-phosphorylated T3E-5P DNA a solution of the corresponding unphosphorylated T3E-NH$_2$ is used.

The sample treated in this way is subsequently incubated also for hybridization with a S3E-Fl DNA solution as disclosed in Example 1.

Under the fluorescence microscope, no fluorescence can be detected for a sample treated in this way. This shows that in nucleic acids that are not terminally modified with anionic groups, like phosphate in the instant case, there is no incorporation into the oxide layer that grows by anodic polarization. This Example proves that the phosphate groups of the sugar phosphate backbone present in the T3E-NH$_2$ DNA are not available for a stable incorporation into the oxide layer that this newly formed by electrochemical polarization.

EXAMPLE 5

This is carried out in the same way as Example 1 with the difference that for anodic polarization a solution of the unphosphorylated fluorescent S3E-Fi is used instead of the 5'-phosphorylated T3E-5P DNA.

A successful immobilization in this case should be detectable directly by fluorescence of the immobilized individual strand. The subsequent hybridization step with fluorescein-marked DNA is therefore not carried out.

Under the fluorescence microscope no fluorescence can be detected in a sample treated in this way. In order to determine whether the lack of fluorescence is caused by incorporation of the fluorescein molecule into the surface at too deep a level, the composition of the oxide layer formed on the sample surface was analyzed by photoelectron spectroscopy (XPS). Up to a depth of 5 nm no phosphorus was detected. The negative result of the phosphorus detection shows that no nucleic acid was bonded.

The results of the described examples and the results of additional comparative examples are compiled in the following table.

TABLE 1

| example No. | oligo-nucleotide[1] | pH[1] | anodic polarization[2] | hybrid-ization[3] | fluores-cence | XPS[4] |
|---|---|---|---|---|---|---|
| 1 | T3E-5P | 4 | +[5] | + | + | n.d.[5] |
| 2 | T3E-5P | 4 | −[5] | + | − | n.d. |
| 3 | S3E-Fl | 4 | − | − | − | n.d. |
| 4 | T3E-NH$_2$ | 4 | + | + | − | n.d. |
| 5 | S3E-Fl | 4 | + | − | − | − |
| 6 | S3E-Fl | 7.5 | + | − | − | n.d. |
| 7 | S3E-Fl | 7.5 | − | − | − | n.d. |
| 8 | S3E-Fl | 7.5[6] | − | − | − | n.d. |
| 9 | S3E-Fl | 7.5/4[7] | + | − | − | − |

[1]for immobilization
[2]as disclosed in Example 1
[3]with S3E-Fl at pH 7.5, as described in Example 1
[4]XPS = photoelectron spectroscopy, compare Example 5
[5]+ = yes; − = no; n.d. = not determined
[6]with additional 10 mmol/liter MgCl$_2$ in the solution
[7]first incubation with additional 10 mmol/liter MgCl$_2$ in the solution at pH 7.5 and subsequent anodic polarization at pH 4

The comparative Examples 6 to 9 were carried out in accordance with the Examples 1 through 5 described in detail with a sample of TiAl6V4, the differences being listed in the table. The conditions under which the immobilization, i.e., incubation with DNA, was carried out are shown in column 2 and those of the optional subsequent anodic polarization are listed in column 3. Columns 4 and 5 indicate whether an anodic polarization and a hybridization with a complementary DNA were carried out. In columns 6 and 7 the results of fluorescence microscopy or photoelectron spectroscopy (XPS) are listed.

In summarizing the above, the embodiments and the parameter compilation in table 1 demonstrate that:

Nucleic acids cannot be immobilized by adsorption on a TiAl6V4 surface in detectable amounts (examples 2, 3, 7, 8).

5'-phosphorylated nucleic acids can be stably immobilized by anodic polarization at pH 4.0 on a TiAl6V4 surface and the 3'-terminal molecule areas are freely accessible for subsequent hybridization (Example 1);

Nucleic acids that are not terminally phosphorylated cannot be immobilized by anodic polarization at pH 4.0 on a TiAl6V4 surface in detectable amounts (examples 4, 5, 6, 9).

LIST OF EMPLOYED REFERENCE CHARACTERS 1 thin oxide layer on the substrate surface
2 oxide layer newly formed by anodic polarization
3 nucleic acid strand to be immobilized
4 complementary nucleic acid strand
F fluorescein
P phosphate

What is claimed is:

1. A metallic object comprising a coating that is comprised of a thin metal oxide layer and nucleic acid compounds selected from the group consisting of nucleic acids and nucleic acid derivatives, wherein the nucleic acid compounds have 5'-terminal or 3'-terminal ends with a covalently bonded anionic group, selected from the group consisting of phosphate, phosphonate, and sulfonate, and wherein the nucleic acid compounds each are bonded to the thin metal oxide layer through the covalently bonded anionic group of the 5'-terminal or 3'-terminal ends and the remainder of the nucleic acid compounds extends away from the thin metal oxide layer, wherein the 5-terminal or 3'-terminal ends are embedded in the metal oxide layer grown about the 5'-terminal or 3'-terminal ends.

2. The object according to claim 1, wherein the unincorporated areas of the nucleic acid compounds that are not incorporated into the metal oxide layer are freely accessible for subsequent interactions with other molecules.

3. The object according to claim 1, wherein the metal of the metallic object is a valve metal or a valve metal alloy.

4. The object according to claim 1, wherein the metal of the metallic object is selected from the group consisting of aluminum, titanium, tantalum, zirconium, niobium, and an alloy of one or more of the metals.

5. The object according to claim 4, wherein the alloy is an intermetallic phase.

6. The object according to claim 1, wherein the nucleic acid compounds are selected from the group consisting of deoxyribonucleic acids (DNA), ribonucleic acids (RNA), peptide nucleic acids (PNA), locked nucleic acids (LNA), and mixed molecules of DNA, RNA, PNA, and LNA.

7. The object according to claim 1, wherein the nucleic acid compounds have modifications of the sugar phosphate backbone caused by modifying agents, wherein the modifying agents are selected from the group consisting of phosphothioates, O-methyl groups, and unconventional bases.

8. The object according to claim 1, wherein the nucleic acid compounds are present at least partially as individual strands.

9. The object according to claim 8, further comprising additional nucleic acid strands bonded by complementary base pairs to the individual strands.

10. The object according to claim 9, wherein the individual strands immobilized on the metal oxide surface and the additional strands are covalently bonded.

11. The object according to claim 9, further comprising active ingredients selected from the group consisting of inorganic molecules, organic molecules, biochemical molecules, cell components, and tissue components, wherein the active ingredients are bonded to the additional nucleic acid strands.

12. The object according to claim 11, wherein the inorganic molecules or organic molecules comprise radioactive elements.

13. A method for manufacturing a metallic object according to claim 1, the method comprising the steps of:
   contacting a metallic substrate surface with nucleic acid compounds having anionic groups 5'-terminal or 3'-terminal ends with a covalently bonded anionic group, selected from the group consisting of phosphate, phosphonate, and sulfonate, and metastably fixing the nucleic acid compounds through the covalently bonded anionic groups on the metallic substrate surface by regiospecific interactions such that the remainder of the nucleic acid compounds extends away from the metallic substrate;
   simultaneously or subsequently, anodically polarizing the metallic substrate surface in an electrolyte solution and growing a metal oxide layer about the 5'-terminal or 3'-terminal ends and embedding the 5'-terminal or 3'-terminal end in the metal oxide layer.

14. The method according to claim 13, wherein a pH value and an ion strength are provided at which the anionic groups are negatively charged and the metallic substrate surface has at least locally some positive charge centers.

15. The method according to claim 14, wherein the pH value is in a range between 3.0 and 5.0.

16. The method according to claim 13, wherein a potential in the step of anodically polarizing is limited to a value between 2 and 200 $V_{SCE}$ so that a sufficiently stable incorporation of the nucleic acid compounds into the metal oxide layer is provided but growth of the metal oxide layer into a recognition area of the nucleic acid compounds required for other processes is prevented.

17. A method for immobilizing complementary nucleic acid compounds selected from the group consisting of nucleic acids and nucleic acid derivatives on a metallic object according to claim 1, the method comprising the steps of:
   selecting a pH value and an ion strength such that the metal oxide layer of the metallic object is negatively charged and a nucleic acid backbone of the nucleic acid compounds of the coating of the metallic object is negatively charged or not charged.

18. The method according to claim 17, wherein the ion strength is in a range of 0.1 to 1.5 mol/liter and the pH value is in a range of pH 5.5 to 8.5.

19. The method according to claim 17, further comprising active ingredients selected from the group consisting of inorganic molecules, organic molecules, biochemical molecules, cell components, and tissue components, wherein the active ingredients are bonded to the nucleic acid compounds.

20. The method according to claim 19, wherein the inorganic molecules or organic molecules comprise radioactive elements.

* * * * *